United States Patent [19]

Zierdt et al.

[11] Patent Number: 5,453,687
[45] Date of Patent: Sep. 26, 1995

[54] METHOD AND A DEVICE TO DETERMINE THE SPATIAL ARRANGEMENT OF A DIRECTIONALLY SENSITIVE MAGNETIC FIELD SENSOR

[76] Inventors: Andreas Zierdt, Thiestr. 11; Bahne Carstens, Nelkenweg 8, both of D-37120 Bovenden, Germany

[21] Appl. No.: 173,898

[22] Filed: Dec. 27, 1993

[30] Foreign Application Priority Data

Jan. 12, 1993 [DE] Germany ............................ 43 00 529.2

[51] Int. Cl.$^6$ ...................................................... G01B 7/14
[52] U.S. Cl. ...................................... 324/207.17; 128/777
[58] Field of Search ........................... 324/207.17, 207.92, 324/207.23, 207.26; 128/777; 343/463, 464, 459

[56] References Cited

U.S. PATENT DOCUMENTS

| | | | |
|---|---|---|---|
| 4,303,077 | 12/1981 | Lewin et al. | 128/777 |
| 4,447,207 | 5/1984 | Kataoka et al. | 128/777 |
| 4,595,022 | 6/1986 | Schorr | 128/777 |
| 4,661,773 | 4/1987 | Kawakita et al. | 324/207.23 |
| 4,765,345 | 8/1988 | Adib | 128/777 |
| 4,776,348 | 10/1988 | Bando et al. | 128/777 |
| 4,788,987 | 12/1988 | Nickel | 324/207.15 |

Primary Examiner—Sandra L. O'Shea
Assistant Examiner—Roger Phillips
Attorney, Agent, or Firm—Hopkins & Thomas

[57] ABSTRACT

A method and a device to determine the spatial arrangement of a directionally sensitive magnetic field sensor, in particular a coil (10) or a Hall probe, in which a number of reference coils (3 to 8) forming a frame of reference are used to generate distinguishable magnetic fields, in which signals induced in the magnetic field sensor (10) by the magnetic fields are measured and in which the spatial arrangement of the magnetic field sensor (10) is determined from the measured signals emitted by the individual reference coils (3 to 8) in which the six reference coils (3 to 8) are arranged to form a three-dimensional frame of reference and in which the position vector of each reference coil cannot be represented as a linear combination with positive factors of the position vectors of the other five reference coils (3 to 8) and in which the scalar product of any position vector in the frame of reference with the position vectors of all six reference coils (3 to 8) vanishes for a maximum of three reference coils, and that the direction vector of the magnetic field sensor (10) is determined from the six measured signals, induced by the six reference coils.

10 Claims, 2 Drawing Sheets

5,453,687

1

METHOD AND A DEVICE TO DETERMINE THE SPATIAL ARRANGEMENT OF A DIRECTIONALLY SENSITIVE MAGNETIC FIELD SENSOR

FIELD OF THE INVENTION

The invention is related to a method and a device to determine the spatial arrangement of a directionally sensitive magnetic field sensor, in particular a coil or a Hall probe, in which a number of reference coils forming a frame of reference are used to generate distinguishable magnetic fields, in which signals induced in the magnetic field sensor by the magnetic fields are measured, and in which the spatial arrangement of the magnetic field sensor is determined from the signals measured emitted from the individual reference coils. This method as well as a corresponding device to practice the method, may for instance be used to register the movements of the tongue in the oral cavity while speaking in order to study speech impediments. There is a large number of further applications, not accessible by optical means that have to be registered and/or monitored in which this method and device may be used.

BACKGROUND OF THE INVENTION

A known device for the implementation of the method described above is the product "Articulograph AG100" made by Carstens Medizinelektronik GmbH, Göttingen, Germany, which was developed in collaboration with the University of Göttingen. This known device is used to register the speech movements in the oral cavity having a helmet on which three reference coils are arranged. The reference coils are aligned perpendicular and parallel to each other in a measuring plane. Ideally, the measuring plane coincides with the center plane of the head of a person wearing the helmet. The oral cavity of the head is spaced at an approximately equal distance from all three reference coils in this case. The three reference coils are used to generate three different alternating magnetic fields, which are distinguishable by different frequencies. A coil used as a directionally sensitive magnetic field sensor is attached in the oral cavity, for example to the tongue of the person wearing the helmet, the spatial arrangement of which is registered, in order to register the speech movements of the person wearing the helmet. The alternating voltage induced in the coil by the alternating magnetic fields of the reference coils is then measured with the aid of a measuring device. The measuring device distinguishes and separates the alternating voltages induced by the individual alternating magnetic fields by their frequencies. An evaluation device is also provided which determines the spatial arrangement of the coil in the oral cavity from the measured alternating voltages. At first the distance between the coil and the respective reference coils is determined from the absolute values of the individual induced voltages. A position vector results from the three distances of the coil to the three reference coils in the oral cavity. The position vector is actually overdetermined by this, as long as it lies in the center plane of the head of the person wearing the helmet, i.e. in the measuring plane, in which the three reference coils are arranged. In principle two reference coils would suffice to determine the position vector of the coil in this plane. This is only valid, though, as long as the coil in the oral cavity is aligned exactly parallel with respect to the reference coils. As soon as the coil has a direction vector diverging from this position, the alternating voltage induced in the coil decreases in spite of an unchanged distance to the reference coils which the measuring unit cannot distinguish from an increasing distance of the coil to the reference coils. But since the supposed distance of the coil to all three reference coils increases by the same factor as a result of this tilting, a compensation of this factor in the known device for registering speech movements, by the overdetermination described above, is possible. As long as an exact parallel alignment of the coil to the reference coils would be ensured, a lateral deviation of the coil from the measuring plane could be observed with this known device. This would cause a relatively large error, though, since the distance of the coil to the reference coils varies only slightly during a movement perpendicular to the measuring plane.

SUMMARY OF THE INVENTION

It is the object of the invention to provide a method and a device to determine the spatial arrangement of a directionally sensitive magnetic field sensor in which any arrangement of the magnetic field sensor in the measuring space can be fully determined. Among other things, more independence from the orientation of the magnetic field sensor while registering speech movements as well as the possibility of a three dimensional registration of the speech movements is achieved.

A method of the type described above, which realizes the object of the invention, has six reference coils arranged to form a three-dimensional frame of reference, in which the position vector of each reference coil cannot be represented as a linear combination with positive factors of the position vectors of the five other reference coils, and in which the scalar product of any position vector in the frame of reference with the position vectors of all six reference coils vanishes for a maximum of three reference coils, and that the direction vector of the magnetic field sensor is determined from the six measured signals induced by the six reference coils. The new method thus achieves a complete registration of the arrangement of the magnetic field sensor with respect to its position, as well as with respect to its orientation. A total of six reference coils emitting distinguishable magnetic fields are provided. The reference coils are arranged in a three-dimensional frame of reference around the magnetic field sensor, by which a measuring space is created in between the reference coils. The requirement that the position vector of each reference coil cannot be represented by a linear combination with positive factors of the position vectors of the other five reference coils is fulfilled by an even distribution of the reference coils around the measuring space. This is necessary in order to achieve a registration of the position of the magnetic field sensor with respect to all directions with as little error as possible. The second requirement, that the scalar product of any direction vector in the measuring space with the direction vectors of all six reference coils vanishes for a maximum of three reference coils, on the other hand, ensures that there are always at least signals from three reference coils to determine the position of the magnetic field sensor. No signal is induced in the magnetic field sensor, e.g. a coil, when the direction vector of its major axis is perpendicular to the respective reference coil, i.e. when the direction vector of the magnetic field sensor and the direction vector of the reference coil have a vanishing scalar product. In the event that signals are actually induced in the magnetic field sensor by only three reference coils, the exact orientation of the magnetic field sensor results because then its direction vector is perpendicular to the direction vectors of the three other reference coils, so that the signals induced by the remaining three reference coils suffice to completely determine the arrangement of the magnetic field sensor.

The position vector and the direction vector of the magnetic field sensor may be determined from the six measured signals and six field equations of the reference coils from a Newton-method, in which for each step of the iteration the Jacobi-matrix in the point of origin of the frame of reference for a fixed direction vector is used. The determination of the position vector and the direction vector of the magnetic field sensor from the six measured signals induced by the six reference coils corresponds to a solution of a homogeneous system of equations with six nonlinear equations, which each are dependent on the position vector as well as the direction vector of the magnetic field sensor. The solution of the system of equations, which is unique with the method described here, is determined advantageously by a numerical iteration. For this a well known Newton-method is applied, in which, to further simplify matters, only the Jacobi-matrix in the point of origin of the frame of reference for a fixed direction vector is used. The elements of the Jacobi-matrix are the partial derivatives of the six field equations of the six reference coils with respect to the three components of the position vector and the three components of the direction vector of the magnetic field sensor. This means that the Jacobi-matrix is a 6×6-matrix with fixed elements for all steps of the iteration of the Newton-method. A further discussion of the Newton-method does not seem necessary at this point, since it is in principle a known process.

In many cases it proves to be critical, though, to ensure the convergence of the Newton-method. In this new method the determination of the spatial arrangement of a directionally sensitive magnetic field sensor is ensured by using the zero position vector and a direction vector linearly combined from the six measured signals and the six direction vectors of the six reference coils as starting values for the Newton-method. It is understood that usually the absolute values of the measured signals of the above mentioned homogeneous linear system of equations, as well as when determining the starting value discussed here, must be adjusted to the field equations of the reference coils with a correction or adjustment factor which is dependent on different but constant external conditions. The correction or adjustment factor has to take into account, for example, the inductivity of a coil used as the directionally sensitive magnetic field sensor and the amplification factor of the measuring device.

A device for the determination of the spatial arrangement of a directionally sensitive magnetic field sensor, in particular a coil or a Hall probe, to practice this method will have a number of reference coils forming a frame of reference to generate distinguishable magnetic fields, a measuring device for measuring and distinguishing signals induced in the magnetic field sensor by the magnetic fields, and an evaluation device for the determination of the spatial arrangement of the magnetic field sensor from the measured signals emitted from the individual reference coils. The object of the invention is realized by providing six reference coils arranged to form a three-dimensional frame of reference, in which the position vector of each reference coil cannot be represented as a linear combination with positive factors of the position vectors of the other five reference coils, and in which the scalar product of any direction vector in the frame of reference with the direction vectors of all six reference coils vanishes for a maximum of three reference coils, so that the position vector and the direction vector of the magnetic field sensor can be determined from the six measured signals induced in the magnetic field sensor by the six reference coils.

For both the method and the device of this invention it is advantageous that the position vectors of the reference coils form two orthogonal systems in which each position vector from one system is linearly dependent on one position vector from the other system. This means for example that the position vectors of one orthogonal system will point in the positive directions and the position vectors of the other orthogonal system will point in the oppositely directed negative directions. The advantage of this arrangement is that the reference coils are evenly distributed over the solid angle of the measuring space and that all arrangements of the magnetic field sensor in the space are registered with an equal dependability.

It is most advantageous, though, to choose the position vectors so that the position vectors of the reference coils form two orthonormal systems which differ only in the sign of the respective position vectors. In this case the position vectors of the reference coils terminate on the surface of a sphere surrounding the measuring space and the arrangement of the reference coils is equi-distant in an ideal way.

Concerning the direction or directional vectors, an arrangement is preferable wherein the directional vectors form two orthonormal systems, in which each direction vector from one system is an equally weighted linear combination of two direction vectors from the other system. In this arrangement the direction vectors of the reference coils, too, are widely and evenly spaced. The signs of the individual direction vector are not of importance since they are not relevant for the vanishing of the scalar products between the direction vector of the magnetic field sensor and the direction vectors of the reference coils.

A further criterium for a favorable arrangement of the reference coils is that the scalar product of the position vector and the direction vector vanishes for each reference coil. This is especially important, insofar as this simplifies and unifies the field equations in the measuring space considerably. This also yields a further symmetry of the arrangement of the reference coils, which also leads to a simplified evaluation process.

The magnetic fields of the reference coils may be alternating fields coded by the use of different frequencies, as is the case with the known two-dimensional method that uses three reference coils and one coil as a directionally sensitive magnetic field sensor. It is also possible to provide the magnetic fields of the reference coils as alternating fields coded by the use of different phases. Both of these last two preferred embodiments are best suited for the use of a coil as the directionally sensitive magnetic field sensor. This only shows alternating magnetic fields through the induced voltage anyway. In contrast to this a scanned operation of the individual reference coils with constant, during the respective registration of signals, and unchanging magnetic fields is preferred when a Hall probe is used as the directionally sensitive magnetic field sensor, even though the time resolution during the determination of the spatial arrangement of the Hall probe is more confined.

It goes without saying that the new method and the new device are also suited to determine the spatial arrangement of more than one directionally sensitive magnetic field sensor simultaneously.

BRIEF DESCRIPTION OF THE DRAWINGS

The invention is further explained and described with the aid of a preferred embodiment. The Figures show.

DETAILED DESCRIPTION

Figure 1:
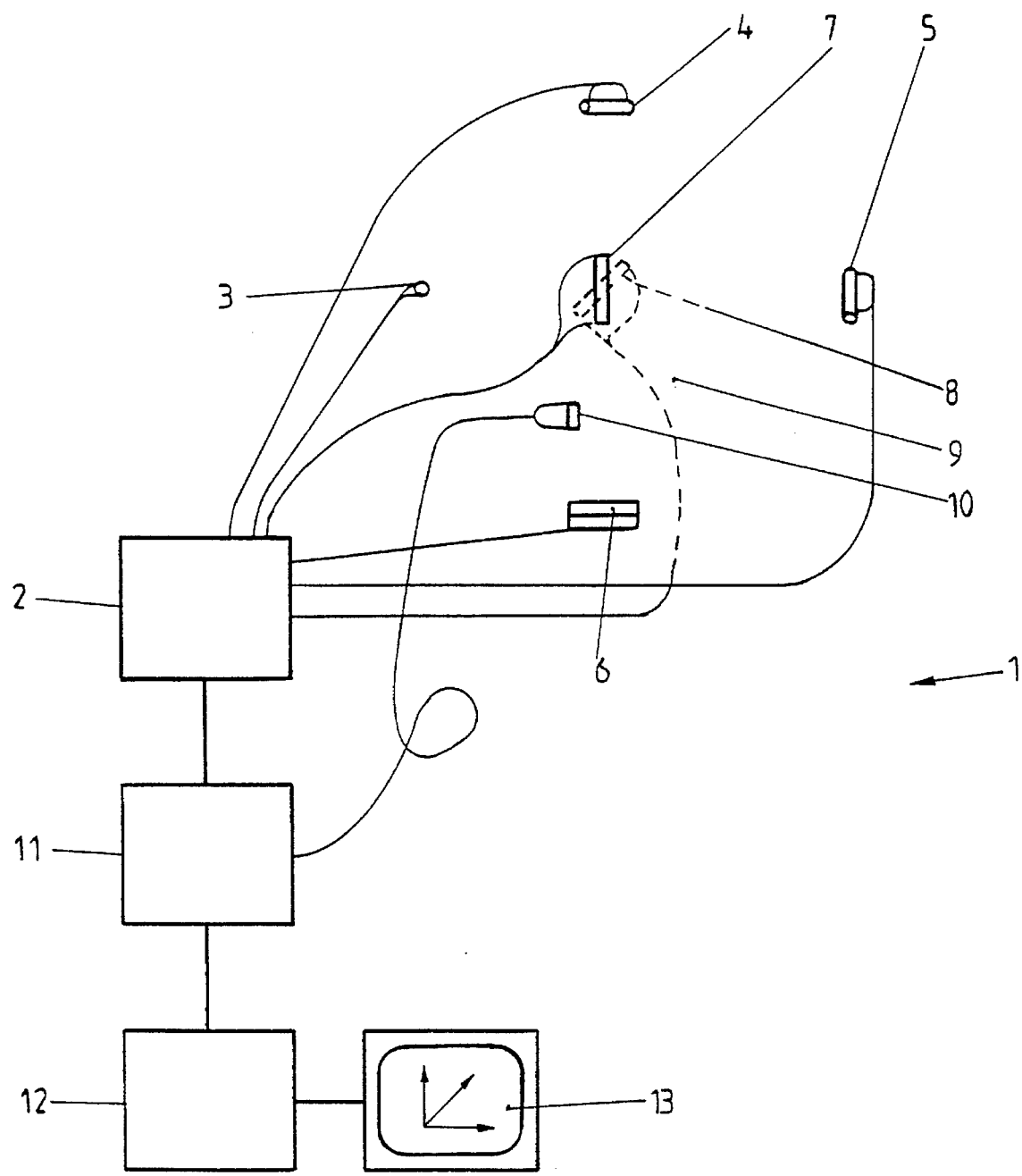
FIG. 1 a schematic drawing of the device to determine the spatial arrangement of a directionally sensitive magnetic field sensor, and FIG. 2 the arrangement of the reference coils of the device according to FIG. 1 in a perspective representation.

The device 1 according to FIG. 1 has an a.c. source 2, which supplies six reference coils 3 to 8 with different a.c. voltages, so that the reference coils 3 to 8 emit six distinguishable, alternating magnetic fields. The reference coils 3 to 8 form an orthogonal frame of reference for a measuring space 9 that is limited in all six directions by one reference coil 3 to 8 each. Within the measuring space 9 the device 1 is able to determine the arrangement of a coil 10 as a directionally sensitive magnetic field sensor with respect to its position, as well as with respect to its orientation. A measuring device 11 picks up the signals from coil 10, which are a.c. voltages corresponding to the alternating fields induced in the coil 10 by the reference coils 3 to 8, and assigns these to each of the respective reference coils. To accomplish this measuring device 11 is connected to the a.c. source 2. From the individual signals measured by measuring device 11 an evaluation device 12 determines the arrangement of the coil 10 in the measuring space 9 in the form of a position vector (x, y, z) and a direction vector (a, b, c). The position vector and the direction vector are then graphically displayed by the evaluation device 12 on a screen 13. The measuring method of device 1 is based on the fact that the signal induced in the coil 10 with respect to the alternating voltage making up the signal changes in relation to each reference coil 3 to 8 when the distance of the coil 10 increases with respect to the reference coil, or when the orientation of coil 10 changes relative to the direction vector of the reference coil.

Accordingly each measured signal contains information about the position vector and the direction vector of the coil 10. But the sum of all this information is sufficient only when two criteria are observed when arranging the reference coils 3 to 8. First of all the position vector of each reference coil may not be represented as a linear combination with positive factors of the position vectors of the other five reference coils. This must only be fulfilled in relation to one endpoint of the position vectors, which always lies within the measuring space 9 due to the interactions of the criterium. Second, the scalar product of any direction vector in the measuring space 9 with the direction vectors of all six reference coils 3 to 8 may vanish in a maximum of three reference coils. Otherwise the scalar product of the direction vector of the coil 10 and the direction vector of more than three reference coils 3 to 8 could vanish, by which the induced voltages of only two reference coils could be measured with the coil 10. This would not suffice to determine the position vector of the coil 10 which requires that at least three of the measured signals differ from zero. When there are exactly three registerable signals and three vanishing signals the position vector of the coil 10 results from the registerable signals and the direction vector of the coil 10 results from the vanishing signals.

Figure 2:
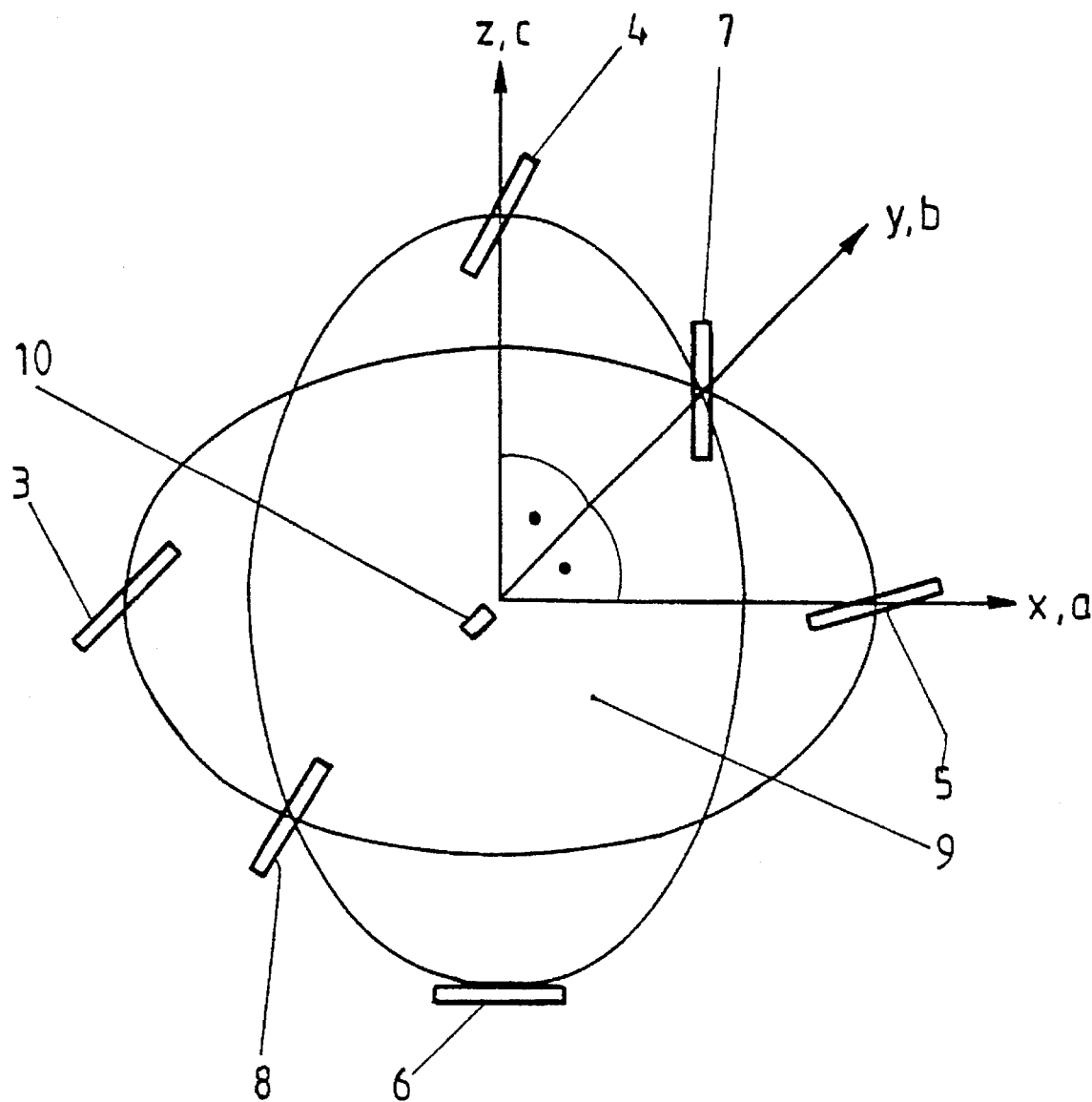

An especially advantageous arrangement of the reference coils 3 to 8 is shown in FIG. 2. Also shown is an orthonormal frame of reference, by which the position vectors and the direction vectors of the reference coils 3 to 8 may be expressed as:

| Reference coil | position vector (x, y, z) | direction vector (a, b, c) |
| --- | --- | --- |
| 3 | (−1, 0, 0) | (0, 1, 0) |
| 4 | (0, 0, 1) | (1/√2, 1/√2, 0) |
| 5 | (1, 0, 0) | (0, 1/√2, 1/√2) |
| 6 | (0, 0, −1) | (1, 0, 0) |
| 7 | (0, 1, 0) | (0, 0, 1) |
| 8 | (0, −1, 0) | (1/√2, 0, 1/√2) |

This shows that all reference coils 3 to 8 are arranged on a spherical shell limiting the measuring space. The reference coils 3 to 8 lie tangentially with respect to this sphere. This is mathematically comprehensible in that the scalar product of the position vector and the direction vector vanishes for each reference coil. It can further be seen that the reference coils 5, 7, and 4 mark the positive directions of the orthonormal frame of reference, while the coils 3, 8, and 6 are arranged in the negative directions of the orthonormal frame of reference. In this way no position vector of a reference coil 3 to 8 can be represented by a positive linear combination of the position vectors of the position vectors of the other five reference coils. The fact that any direction vector of the coil 10 has a vanishing scalar product with the direction vectors of a maximum of three reference coils is also readily seen. A special advantage of the arrangement of the reference coils 3 to 8 shown in FIG. 2 is that the reference coils 3 to 8 have the highest symmetry with respect to the end point of their position vectors, the center of the measuring space 9, as well as of their direction vectors. The reference coils are distributed equi-distantly and the alternating magnetic fields of all reference coils at the origin of the frame of reference differ only in their orientation with respect to the origin. This makes the determination of the arrangement of the coil 10 in the measuring space 9 from the induced and measured a.c. voltages decidedly simpler.

A further advantageous arrangement of the reference coils has the following position and direction vectors, in which the designation of the reference coils is in accordance with the position vectors of FIG. 2:

| Reference coil | position vector (x, y, z) | direction vector (a, b, c) |
| --- | --- | --- |
| 3 | (−1, 0, 0) | (0, 1, 0) |
| 4 | (0, 0, 1) | (0, 1/√2, 1/√2) |
| 5 | (1, 0, 0) | (1/√2, 0, 1/√2) |
| 6 | (0, 0, −1) | (1, 0, 0) |
| 7 | (0, 1, 0) | (0, 0, 1) |
| 8 | (0, −1, 0) | (1/√2, 1/√2, 0) |

The reference coils are arranged on a sphere limiting the measuring space in this case, too, but only half of the direction vectors are orientated parallel to the surface of the sphere, while the other half are orientated at an angle of 45° with respect to the surface of the sphere. Favorable symmetry relations are attained insofar as each of the two reference coils assigned to one normal direction form equivalent pairs. The sacrifice of a higher symmetry is compensated for by the fact that, independent of the orientation of the directionally sensitive magnetic field sensor in the measuring space, a non-vanishing signal is induced in the magnetic field sensor by one reference coil in each normal direction. This is explained mathematically by the fact that the scalar product of the position vector and the direction vector of one reference coil vanishes in each normal direction, but that it is not zero for the other reference coil, in that the direction vectors of the two reference coils do not lie in parallel planes, which is the case for the embodiment of FIG. 2. Furthermore the favorable arrangement of the reference coils provides the possibility of an especially elegant evaluation of the signals induced in the magnetic field sensor, since the field equations of all six reference coils can by transmuted in a cyclic fashion by a single operator.

While the foregoing specification and drawings disclose a preferred embodiment of the invention, it will be understood by those skilled in the art that variations and modifications thereof can be made without departing from the spirit and scope of the invention as set forth in the following claims.

| LIST OF REFERENCE NUMERALS | |
|---|---|
| 1 | device |
| 2 | a.c. source |
| 3 | reference coil |
| 4 | reference coil |
| 5 | reference coil |
| 6 | reference coil |
| 7 | reference coil |
| 8 | reference coil |
| 9 | measuring space |
| 10 | coil |
| 11 | measuring device |
| 12 | evaluation device |
| 13 | screen |

We claim:

1. A method for determining the spatial arrangement of a directionally sensitive magnetic field sensor, in particular a coil or a Hall probe, comprising the steps of:

forming a frame of reference between six reference coils;

emitting separate magnetic fields from each of the reference coils:

inducing a signal in the magnetic field sensor by the magnetic field of each reference coil;

measuring the signals induced in the magnetic field sensor;

determining the spatial arrangement of the magnetic field sensor from the measured signals induced in the magnetic field sensor from each of the individual reference coils;

arranging the six reference coils to form said frame of reference as a three-dimensional frame of reference, in which the position vector of each reference coil cannot be represented as a linear combination of the position vectors of the five other reference coils when the position vectors of the linear combination are multiplied by only positive factors, and in which the scalar product of any position vector in the frame of reference with the position vectors of all six reference coils vanishes for a maximum of three reference coils only; and determining the direction vector and the position vector of the magnetic field sensor from the measured signals induced in the magnetic field sensor by the six reference coils.

2. The method of claim 1, further comprising the steps of determining the position vector and the direction vector of the magnetic field sensor from the measured signal induced in the magnetic field sensor, and from a field equation for each one of the six reference coils using a Newton-method, in which for each step of the iteration in the Newton-method the Jacobi-matrix at the point of origin of the frame of reference for a fixed direction vector is used.

3. The method of claim 2, further comprising the step of using the zero position vector and a direction vector linearly combined from each of the measured signals induced in the magnetic field sensor, and from each of the direction vectors, for each of the six reference coils as the starting values for the Newton-method.

4. A device to determine the spatial arrangement of a directionally sensitive magnetic field sensor, in particular a coil or a Hall probe, comprising:

six reference coils forming a frame of reference between the reference coils, each reference coil generating a separate magnetic field;

a measuring device for measuring and distinguishing the signals induced in the magnetic field sensor by each of said magnetic fields;

an evaluation device for the determination of the spatial arrangement of the magnetic field sensor from the measured signals induced in the magnetic field sensor by each of the individual reference coils;

wherein the six reference coils are arranged to form a three-dimensional frame of reference, in which the position vector of each reference coil cannot be represented as a linear combination of the position vectors of the other five reference coils when the position vectors of the linear combination are multiplied by only positive factors, and in which the scalar product of any direction vector in the frame of reference with the direction vectors of all six reference coils vanishes for a maximum of three reference coils only, so that the position vector and the direction vector of the magnetic field sensor can be determined from the measured signals induced in the magnetic field sensor by the six reference coils.

5. The device of claim 4, wherein the position vectors of the reference coils form two orthogonal systems, in which each position vector from one system is linearly dependent on one position vector from the other system.

6. The device of claim 5, wherein the position vectors of the reference coils form two orthonormal systems which differ only in the sign of the respective position vectors.

7. The device of claim 4, wherein the direction vectors of each reference coil form two orthonormal systems, in which each direction vector from one system is an equally weighted linear combination of two direction vectors from the other system.

8. The device of claim 4, wherein the scalar product of the position vector and the direction vector vanishes for each reference coil.

9. The device of claim 4, wherein the magnetic fields of the reference coils are alternating magnetic fields coded by a different frequency for each of the reference coils.

10. The device of claim 4, wherein the magnetic fields of the reference coils are alternating magnetic fields coded by a different phase for each of the reference coils.

* * * * *